United States Patent
Stevelinck

(10) Patent No.: US 9,229,964 B2
(45) Date of Patent: Jan. 5, 2016

(54) DATABASE CLONING AND MIGRATION FOR QUALITY ASSURANCE

(71) Applicant: Visa International Service Association, San Francisco, CA (US)

(72) Inventor: Scott Stevelinck, Lyons, CA (US)

(73) Assignee: Visa International Business Machines Corporation, San Francisco, CA (US)

( * ) Notice: Subject to any disclaimer, the term of this patent is extended or adjusted under 35 U.S.C. 154(b) by 210 days.

(21) Appl. No.: 13/662,182

(22) Filed: Oct. 26, 2012

(65) Prior Publication Data

US 2013/0110770 A1    May 2, 2013

Related U.S. Application Data

(60) Provisional application No. 61/552,287, filed on Oct. 27, 2011.

(51) Int. Cl.
*G06F 7/00* (2006.01)
*G06F 17/30* (2006.01)
*G06Q 50/24* (2012.01)

(52) U.S. Cl.
CPC ........ *G06F 17/303* (2013.01); *G06F 17/30079* (2013.01); *G06Q 50/24* (2013.01)

(58) Field of Classification Search
CPC .................................................. G06F 17/30079
USPC .......................................................... 707/640
See application file for complete search history.

(56) References Cited

U.S. PATENT DOCUMENTS

| | | | |
|---|---|---|---|
| 7,080,102 B2 | 7/2006 | O'Connell | |
| 8,015,157 B2 | 9/2011 | Kamei | |
| 2007/0106629 A1 | 5/2007 | Endacott | |
| 2007/0260830 A1* | 11/2007 | Faibish et al. | 711/162 |
| 2010/0070726 A1* | 3/2010 | Ngo et al. | 711/162 |

FOREIGN PATENT DOCUMENTS

| | | |
|---|---|---|
| WO | 01/97099 A1 | 12/2001 |
| WO | 2011/041516 A1 | 4/2011 |

* cited by examiner

*Primary Examiner* — Ajith Jacob
(74) *Attorney, Agent, or Firm* — Kilpatrick Townsend & Stockton LLP

(57) ABSTRACT

Embodiments of the invention relate to systems and methods for cloning a production database for quality assurance (QA) by the merchant users. A QA user may request tokens, card types and other data associated with a payment device for quality assurance purposes. The payment network redirects the QA request to a go-between database that is present between the QA user and the production environment of the payment network rather than pull the information directly from the production environment. As a result, the merchant is able to use tokens for testing, without violating consumer privacy and security rules and regulations (e.g., PCI rules). The QA user does not have to create a customized testing solution.

20 Claims, 11 Drawing Sheets

DATABASE CLONING AND MIGRATION FOR QUALITY ASSURANCE

CROSS-REFERENCES TO RELATED APPLICATIONS

This application is a non-provisional application of and claims the benefit of priority of U.S. Provisional Application No. 61/552,287, filed on Oct. 27, 2011, which is herein incorporated by reference in its entirety for all purposes.

BACKGROUND

This application relates to the field of data migration, in particular, data migration from a production environment to lower environments. A production environment is mostly used by different entities (organizations, companies, businesses, financial institutions, etc.) for their processing needs using live applications. Lower environments, such as, quality assurance (QA), development, staging, etc., help ensure that the applications are well tested and stable before being migrated to the production environment.

A QA environment is mostly used to test data, hardware and software that closely simulate the production environment. However, in most cases, access to production data in lower environments is limited due to security reasons. A good example is the consumer data for financial transactions (e.g., payment card information), access to which is highly regulated. Payment card industry (PCI) rules and regulations emphasize the policy for privacy and security concerning consumer data. These rules and regulations restrict merchant users from accessing the consumer data and the production infrastructure associated with securing the consumer data for QA purposes. Quality assurance of the financial transaction system is desirable for the seamless operating of commerce. Similar needs for production infrastructure testing exists in other industries such as medical records, criminal records, vehicle driver information, loan applications, stock trading and voter registration, where access to databases containing sensitive information is regulated.

One of the goals for a user performing QA testing is to test the system and environment as much as possible with the least amount of deviations from the final system that is deployed into the production environment. Any deviation from the production environment introduces a proportionally exponential amount of risk associated with the system when introduced in the production environment. For example, merchant users generate customized testing environments to mimic the production systems and databases implemented by a payment system for testing purposes. However, these testing systems deviate from a production system in a variety of known and also unknown ways. For instance, the QA environment may have code introduced at various stages of the system pipeline to emulate interfaces that interact with the payment system. Also, it would be difficult to emulate all the artifacts of the network lag and system architecture of the payment network that are usually not part of any requirements documentation. These deviations increase the risk that when the system is deployed in a production environment that an error or deficiency that was latent due to the deviations introduced by the QA testing environment would manifest itself while the system is in full production and cause significant loss. Another consideration is the cost associated with architecting, designing and maintaining the QA testing environments for the merchant users.

Embodiments of the invention address this and other problems, individually and collectively.

BRIEF SUMMARY

Embodiments of the invention broadly described, allow third party participants partial access to the infrastructure (and information) protected by a custodian of sensitive information while maintaining isolation and privacy for the sensitive information.

Embodiments of the invention relate to systems and methods for cloning a production database for quality assurance by the merchant users. The QA user may request tokens, card types and other data associated with a payment device for quality assurance purposes. The payment network redirects the QA request to a go-between (intermediary) database that is present between the QA user and the production environment of the payment network rather than pull the information directly from the production environment. As a result, the merchant is able to use tokens for testing, without violating consumer privacy and security rules and regulations (e.g., PCI rules). The QA user does not have to create a customized testing solution.

Embodiments of the invention disclose a computer implemented method for migrating a database comprising: polling an intermediary database for a migration request for migrating a first database in a first environment to a second database in a second environment, detecting the migration request in response to the polling, creating a link between the first database and the intermediary database, migrating data from the first database into the intermediary database and removing the link between the first database and the intermediary database, wherein the data from the intermediary database is loaded thereafter into the second database.

One embodiment of the invention discloses a first database server comprising a processor and a computer-readable medium coupled to the processor, wherein the computer-readable medium comprises code executable by the processor for implementing a method for migrating a database, the method comprising: polling an intermediary database for a migration request for migrating a first database in a first environment to a second database in a second environment, detecting the migration request in response to the polling, creating a link between the first database and the intermediary database, migrating data from the first database into the intermediary database, and removing the link between the first database and the intermediary database, wherein the data from the intermediary database is loaded thereafter into the second database.

One embodiment of the invention discloses a computer implemented method for migrating a database comprising: receiving a migration request for migrating a first database associated with a first database server to a second database associated with a second database server, storing the migration request in an intermediary database associated with an intermediary database server, receiving a first query from the first database server for the migration request stored in the intermediary database, storing a snapshot of the first database in the intermediary database in response to the first query, using a link created by the first database server, receiving a second query from the second database server for migrating snapshot data into the second database and migrating the snapshot data from the intermediary database for loading into the second database in response to the second query.

One embodiment of the invention discloses an intermediary database server comprising a processor and a computer-readable medium coupled to the processor, wherein the computer-readable medium comprises code executable by the processor for implementing a method for migrating a database, the method comprising: receiving a migration request for migrating a first database associated with a first database server to a second database associated with a second database server, storing the migration request in an intermediary database associated with the intermediary database server, receiving a first query from the first database server for the migration request stored in the intermediary database, storing a snapshot of the first database in the intermediary database, in response to the first query, using a link created by the first database server, receiving a second query from the second database server for migrating snapshot data into the second database and migrating the snapshot data from the intermediary database for loading into the second database in response to the second query.

These and the other embodiments of the invention are discussed in further detail below.

DETAILED DESCRIPTION

Figure 1:
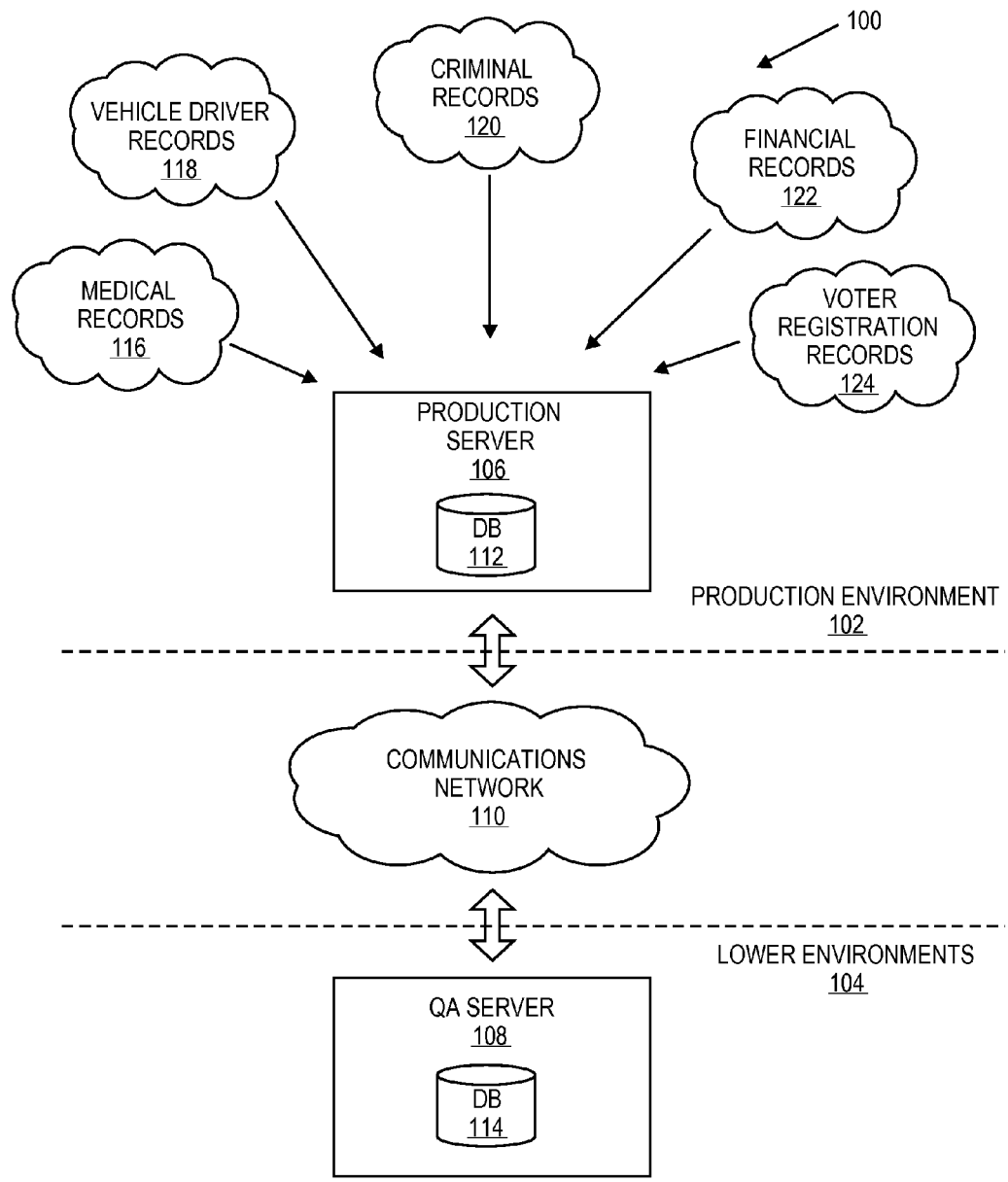
FIG. 1 is a typical system illustrating relationship between a production environment and lower environments.

Prior to discussing embodiments of the invention, description of some terms may be helpful in understanding embodiments of the invention.

"Data Migration" may include transferring a plurality of data from one database to another database. Data migration may be local or remote. Local data migration may include transferring the data between the databases when both the databases may reside on the same server but mapped in separate virtual memories. Remote data migration may include transferring the data from a database residing on one server to another database residing on another server. In remote data migration, the transferring of data may be over a wired or wireless communication link. Data migration may be performed from one environment having a set of privileges (highly restricted) into another environment with another set of privileges (less restricted).

A "link", such as a "database link", may include a connection between a first database and a second database. The link may be used for transferring data between the two databases. A one way link may allow the data transfer only in one direction. In one embodiment, the first database may be a local database and the second database may be a remote database. In some cases proper access permissions may be required by software applications for creating and removing the links between the databases. In one embodiment, a secure link guided by a firewall may be required to transfer sensitive data between the databases.

A "production database" may be used for keeping records of relevant information that may be used in conducting different businesses. For example, a production database for financial transactions may include the information relating to customers, such as, customer personal information, payment device information, etc. A production database may be used for payment transactions, loan applications, money transfer, etc. Similarly, a production database for vehicle registrations may include information relating to vehicle drivers, such as, driver's name, contact information, vehicle information (model, year), etc. Such information may be used for auto insurance, driving records, etc. Production database may have thousands or even millions of records based on the business. In most cases, the production database is protected from third parties for maintaining isolation and privacy of the stored information.

An "intermediary database" may be used as a temporary or a go-between database for storing information and data. In one embodiment, data and information may be stored in the intermediary database such that it may be accessible by multiple environments having different levels of privileges. For example, data may be migrated from a production environment having higher privileges to the intermediary database, where it may be accessed from a QA environment having lower privileges.

A "target environment" may be used for a QA environment for custom testing. The target environment may be specified by a QA user for testing the system and the infrastructure at various stages of the testing. For example, a target environment may be used for functional testing of a production database. Similarly, a target environment may be used for performance testing of the infrastructure, such as stress testing.

A "target database" may include a database in a target environment meeting certain criteria. The criteria may be pre-defined such that the target database is created based on the criteria. For example, in payment systems, a target database may be created only for chargeback transactions. Similarly, a target database may be created with amounts over thousand dollars.

"Quality Assurance" may include means for testing a system or an infrastructure to ensure quality or to ensure that the system or the infrastructure behaves as expected. In some cases, a test suite may be prepared with expected results that should match with the actual results collected after executing the test suite. A QA database may be a database used mainly for QA purposes, i.e., the data in the QA database may be similar to the production database to simulate the real life scenarios during testing. For example, in order to test how a payment network would behave in detecting fraud during payment transactions may require real historical data for customer transactions to detect fraud patterns.

A "snapshot" may include a copy of a database as of the moment the snapshot was created. Snapshots may be used for backups, maintaining historical data for report generations and for testing. A QA user may use a snapshot of a database to run a first round of tests and may revert back to the snapshot for running next level of rounds to have consistent data at the beginning of each round of tests.

A "token" may be a uniquely generated value used in payment networks. A token may be associated with a PAN (Primary Account Number) that may be used with the PAN or in place of the PAN in order to protect the sensitive consumer information to comply with the PCI rules. A token may be a secure token, i.e., mathematically irreversible, so that the token by itself has no useful value for someone with malicious intent. In some cases, a token may retain the last four digits of the PAN as a means of matching the token to the payment card owner. Tokens may be used by merchants for record keeping and future transactions without having to access the PAN for each transaction.

A "card type" may indicate a specific variety of payment card. The specific variety may correspond to a payment processing organization, such as, Visa™, Master card™, Discover™, or American Express™. A payment card number may include card type information in it. It could also relate to specific issuers or specific functionality such as debit, credit or stored value. For example, the first four to six digits of the payment card number may represent the issuer identification number including the card type. As an example, Visa cards may always begin with a number "4", Master cards may have the first two digits in the range "51-55" and American Express cards may always begin with a "34" or "37".

The term "application server" may include a server program in a computer in a distributed network that provides software applications for different services. An example of an application server may be a web server that supports a JAVA platform, Enterprise Edition (JEE). The application server may include a web browser based graphical user interface, a set of applications on a local area network (LAN) and a back-end database and transaction server.

The term "server computer" may include a powerful computer or cluster of computers. For example, the server computer can be a large mainframe, a minicomputer cluster, or a group of servers functioning as a unit. In one example, the server computer may be a database server coupled to a Web server. The server computer may be coupled to a database and may include any hardware, software, other logic, or combination of the preceding for servicing the requests from one or more client computers. The server computer may comprise one or more computational apparatuses and may use any of a variety of computing structures, arrangements, and compilations for servicing the requests from one or more client computers.

The term "client computer" may include any suitable computational apparatus. The client computer may be an apparatus operated by a consumer, a user associated with a merchant, or any other individual. The client computer may use any suitable wired or wireless network, including the Internet, in order to communicate with other systems.

Embodiments of the invention broadly described, allow third party participants partial access to the infrastructure (and information) protected by a custodian of sensitive information while maintaining isolation and privacy for the sensitive information by cloning a database. In many instances, the rules and regulations in the industry require the custodian of the information to maintain isolation between the information and the third party participants. Sensitive information protected by the custodian may include but is not limited to financial information, medical records, criminal records, vehicle driver information, loan applications, stock trading and voter registration.

Embodiments of the invention comprise a multi-stage process that allows the data to be migrated safely and securely to lower environments. One embodiment of the invention includes polling for a request for migrating a first database in a first environment (production) into a second database in a second environment (QA). The request for migration may be initiated by submitting a form by a QA user via a web interface and may include an email address of the requestor and a target (QA) environment. The request with the information provided may be stored in an intermediary database. A data manager module in the first environment periodically polls for migration requests logged in the intermediary database. The data manager module may poll for QA migration requests instead of using interrupts or doorbell events to prevent denial of service attacks from a rogue QA environment or QA user. A denial of service attack would allow a malicious QA user to overwhelm the production environment with requests. Once a request for migration to a target environment is detected, the data manger module creates a one way link from the first database to the intermediary database. The data manager application captures a snap shot of the first database and allows row insertion in the intermediary database. In some embodiments, only a subset of the data from the first database is migrated to the intermediary database to protect the sensitive information. Once the data base is migrated, the one way link is destroyed by the data manager module. Note that creating and removing the one way link may require that the correct permissions exist.

A data loader application in the second environment polls for a migration response to check if a new snapshot needs to be loaded into the target QA environment. The data loader may periodically check for migration requests from the QA user, and if there are no requests pending, the data loader may wait or sleep for a pre-determined duration before checking the status of the migration requests again. The data loader may only load the data in the target QA environment if the request for the target environment was made. The data may be loaded into the target environment using a batch process. Once the data is loaded, a notification is sent to the requestor that the migration is complete.

A single QA user may request different target QA environments for different testing stages. Each target environment may have its own cloned database that the QA user may access for a specific testing stage. Different target environments may include stress testing, fraud rules testing, customer loyalty points testing, chargeback transactions testing, etc. By cloning the database in accordance with embodiments of the invention further allows different merchants to clone the production database in their QA environments for testing specific to their business needs while keeping isolation from each other. For example, a merchant who promotes customer loyalty awards may want to have a target environment to test that feature as compared to another merchant who does not participate in the customer loyalty award program.

Embodiments of the invention are discussed for a payment network system, however, it is understood that the embodiments may be applicable to any system which requires partial access to production data for QA purposes without violating rules and regulations of the related industry.

The production environment is maintained with a high level of security and access control. Strict isolation policies are followed for data and execution environment associated with the production environment. Production data in the production database may include but is not limited to PAN and account type. The intermediary database may reside in the QA environment and may not have direct access to production environment. All connections between QA and production environment may be initiated by the production environment. Production environment controls the links between the production database environment and the QA environment for better security and quality control. The production database may permit a single database link connection from production to the QA environment. In some embodiments, the link may allow only unidirectional flow of data from production environment to the QA environment. These procedural restrictions allow the production environment control of link initiation, isolation from data or executable exploits in the QA environment, and protection from denial of service attacks on the production environment. Additional security measures may be implemented to protect the production database.

The production environment may have tokens associated with a consumer PAN for security reasons. PCI regulations do not allow the sensitive consumer data (for example, PAN) to be accessible in the lower environments. Embodiments of the invention allow replicating the tokens generated in the production environment into the lower environment using a multi-stage process.

Embodiments of the invention isolate the production environment by removing the direct relationship between a secure token and the consumer payment card number. In one embodiment, only the token is migrated to the lower environment and associated with a fake payment card number generated randomly on the fly. The fake payment card numbers may be required to test the payment flow by a QA user in integration with other systems. For example, a call center system integrated with the system tested by the QA user may request for a payment card number to service a request for canceling a payment card account asscociated with that payment card number. In this case, the call center system may provide a token associated with the payment card account and request for the payment card number. The QA user may be able to pull the payment card number based on the token associated with the payment card account from a QA vault database. The fake payment card number can simulate a real payment card number for QA testing.

Having access to the same tokens in the QA environment enables the QA users to perform more realistic testing that is closer to the production environment. For instance, a QA user with a merchant may be testing payment flow that encompasses multiple systems. For example, a QA user may be testing a system that is integrated with another system that processes payments using a third party. The third party may make a request for fake payment card numbers by providing the tokens. The QA user then can take those tokens and decrypt the fake payment card numbers stored in a vault database associated with the token for providing to the other system for checking the payment flow. Thus, having access to the real tokens in the QA environment helps QA users perform realistic testing of the relationship between tokens and the payment card numbers. Embodiments of the invention maybe viewed as first migrating data from the production environment to the QA environment for QA testing by the merchant during a migration phase followed by the testing phase by the QA user (i.e., merchant).

The QA user (merchant) may initiate the migration phase by requesting migration of consumer tokens, account types and other data associated with a payment device for quality assurance purposes. As noted above, account types may include the name of the payment network that services the account. Examples of account types include but are not limited to VISA, MasterCard, AMEX, Discover, Diner's Card, etc. In response to the QA user request, the information from the database is migrated to a QA environment database that is now accessible to the QA user. In one aspect, the token and account type are migrated from the production environment database to the QA environment database via the intermediary database and associated with a substitute (or fake) PAN. The substitute (or fake) PAN is generated based on the account type associated with the token. For instance, an AMEX PAN number maybe 15 digits long as compared to a VISA or MasterCard PAN number, which may be 16 digits long. Similarly, many VISA PAN numbers start with the alphanumeric digit 4, while MasterCard PAN numbers start with the alphanumeric digit 5. Therefore, the substitute (or fake) PAN is generated to comply with the format of the account type associated with a particular token.

The migration request from the QA user may also contain a target environment. During the testing phase, the QA user accesses the QA target environment database located at the payment network instead of the production environment database for testing. For the merchant, one of the goals for the QA testing is to subject the system to as many stress situations as may be possible in a production system. Cloning the database on the payment network side with real tokens associated with account types has the advantage of generating scenarios that are much closer to the production environment over the traditional means of simulating the production environment. Embodiments of the invention provide multiple advantages that are discussed below using a number of simplistic examples.

In one example, embodiments of the invention may help in detecting data corruption errors. A data corruption error may manifest due to a variety of reasons anywhere in the system including the request queues in the merchant's QA environment, the network connecting the merchant and the payment network and the payment network itself. If the data corruption error converts a valid token to an invalid token, the QA target environment located at the payment network would respond with an error since the payment network will not have a valid entry for the invalid token, thus flagging an error in the system. The same error would be masked and silently corrupt data in a test system that was architected to respond to arbitrary tokens with fake PAN's, without checking the validity of the tokens against real tokens.

Embodiments of the invention may also provide an advantage in stress testing the system. The number of requests and the request types maybe altered to stress the infrastructure during QA testing. For instance, a particular test maybe designed to test a heavy load scenario where the system maybe significantly stressed due to a shopping holiday such as Black Friday with millions of transactions occurring almost simultaneously. Such a scenario may expose the deficiencies in the system that may include inadequate depth (capacity) of the database or network queues, problems with the network connection between the merchant network and the payment network, and network bandwidth issues between the merchant network and the payment network. Inability to connect to a payment network during a peak sale period could result in significant losses for the merchant. Without a real network connection from the merchant to the payment network many aspects of the system such as the network and security protocol between the merchant and the payment network, the network bandwidth and the connection types and any undocumented assumptions on either the merchant or the payment network side are difficult to test and exposes the merchant to additional risk of failure.

Embodiments of the invention further provide an advantage by validating different algorithmic paths. In response to the request from the merchant, the payment network may respond with a substitute (or fake) PAN number based on the account type associated with the token. There may be several dependencies built into the merchant environment that reacts to the format of the PAN number returned from the payment network. For instance, PANs associated with a first payment processing network may be processed differently than PANs associated with a second payment processing network. The merchant may or may not have the association of a particular token with the associated account type stored in their database. Therefore, running tests from the merchant's QA environment that receives the response to the PAN requests and processes the response has the advantage of testing all the paths associated with the different account types associated with real sets of tokens.

The above examples highlight only a few of the advantages of using a cloned database from the payment network side instead of using emulated interfaces or data that is not associated with real the consumer information.

FIG. 1 is a typical system illustrating relationship between a production environment and lower environments.

A typical system 100 illustrates a production environment 102 and lower environments 104 configured to communicate using a communications network 110. Production environment 102 may include a production server 106 with a production database 112. Lower environments 104 may be hosted on a QA server 108 with a QA database 114.

The production database 112 may store a plurality of data and information. As illustrated in the figure, the production database 112 may include medical records 116, vehicle driver records 118, criminal records 120, financial records 122, voter registration records 124 or similar records. It is understood that different types of records may be stored in different databases associated with one or more servers; however, for illustrative purposes only one database is shown. Some of the records may include sensitive data that may be protected by the rules and regulations of the related industry.

Lower environments 104 may include a QA environment where the system (data, software, hardware) may be tested before migrating to the production environment to ensure that the system and the infrastructure have been tested completely before going live. Lower environments 104 may also include a stage/pre-production environment where final changes to the production database are stored or a copy of the production database is stored, should the production database fail for some reason.

Access to the data and information stored in the production database 112 may be required in the lower environments 104 for various reasons. For example, in the QA environment, it is desirable for a QA user performing the QA testing to test the system and the infrastructure as much as possible with the least amount of deviations from the final system that is deployed in to the production environment 102. In most case, a QA user may be restricted to directly interact with the production environment 102 but may have enough privileges in the QA environment. The production environment 102 may have the highest level of security and lowest level of privileges from the end-user, QA user or merchant's perspective. Embodiments of the invention allow partial access to the production data in a secure manner by cloning the production database in the lower environments, as discussed with the help of FIG. 2.

Figure 2:
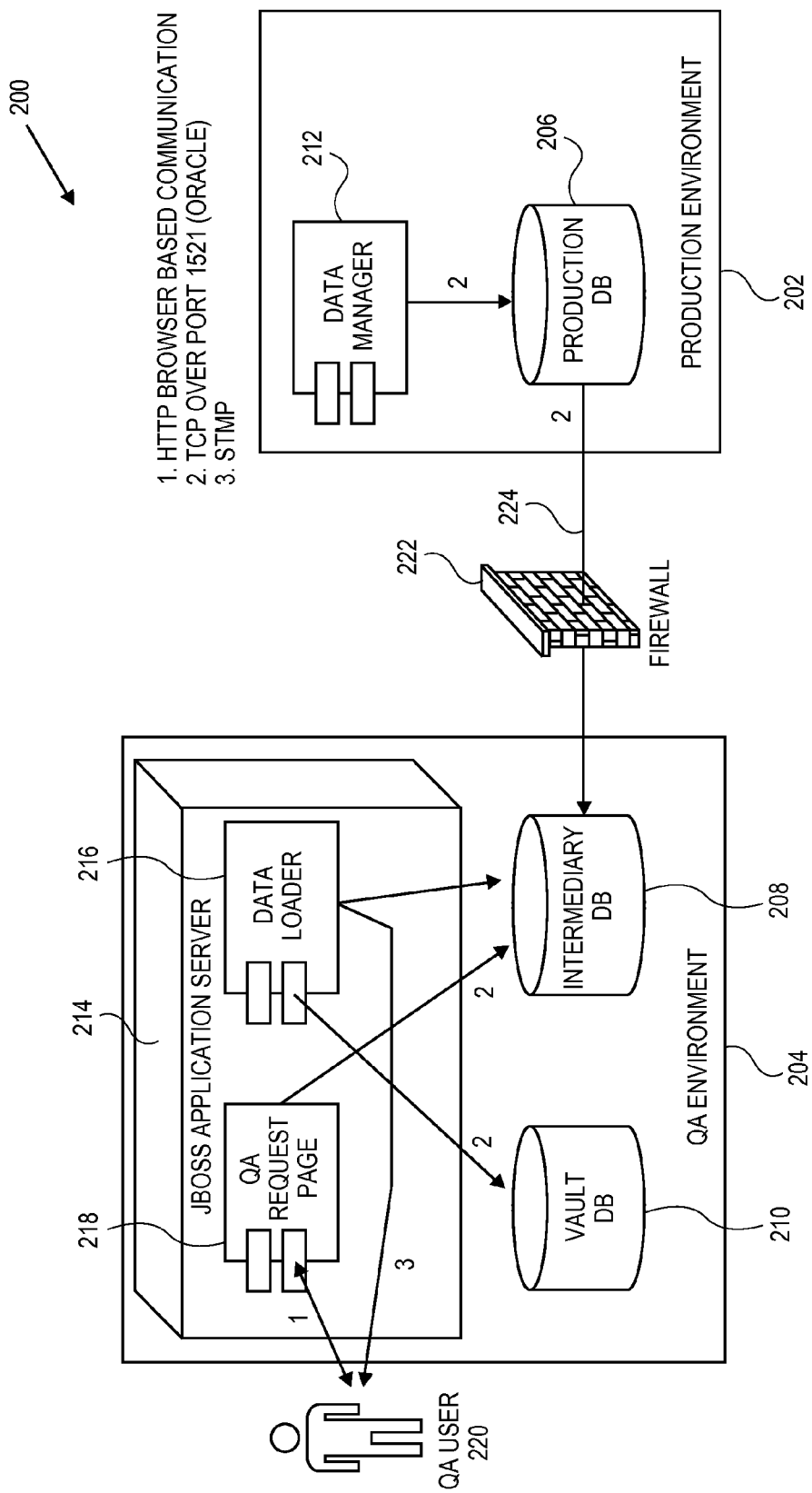
FIG. 2 is a system illustrating a non-limiting embodiment of the invention for cloning a production database in a target environment for quality assurance.

FIG. 2 illustrates an embodiment of the invention for data migration from a production environment to a QA environment.

A QA user 220 may provide a request for database migration from a production environment 202 to a QA environment 204 for quality assurance purposes. The QA user 220 may have enough privileges to generate a migration request in the QA environment 204 but may be restricted from directly interacting with the production environment 202. The production environment 202 and the QA environment 204 may be physically isolated from each other for better security. A production database 206 may have production data requiring highest level of security and lowest level of privileges from the QA user 220. In one embodiment, the production database 206 includes a plurality of records for customer payment card information (PAN, token, card type, etc.) and customer personal information (name, billing address, shipping address, etc.) for financial transactions. In other embodiments, the production database 206 may include medical records 116, vehicle driver records 118, criminal records 120, financial records 122, voter registration records 124 or similar records requiring restricted access by the QA user 220.

Embodiments of the invention clone the production database 206 into an intermediary DB 208 by migrating only a subset of data to the QA environment 204. In one embodiment, only the token and the card type is passed to the QA environment 204 but not the customer PAN to comply with the PCI rules. The intermediary DB 208 may reside in the QA environment 204 and may not have direct access to the production environment 202. All connections between the production environment 202 and the QA environment 204 may only be initiated by the production environment 202 and may be further guided using a firewall 222. The production database 206 may only permit a one way link to allow unidirectional flow of data from the production environment 202 to the QA environment 204. A system administrator may establish access list at the firewall 222 for allowing unidirectional flow between the production environment 202 and the QA environment 204. The link between the production environment 202 and the QA environment 204 may use Transmission Control Protocol (TCP). TCP is one of the main protocols in TCP/IP networks that enables two hosts to establish a connection and exchange streams of data. For example, in an Oracle database, a data link may use TCP over port 1521.

A module called data manager 212 in the production environment 202 may be configured to take a snap shot of the production database 206 and migrate it in to the intermediary DB 208 using the one-way link 224. A module called data loader 216 in the QA environment 204 may extract the snapshot data from the intermediary DB 208 and load it into a vault (QA) DB 210 that can be accessed by the QA user 220 for QA purposes. In one embodiment, TCP over port 1521 may be used for accessing the production database 206, the intermediary DB 208 and the vault DB 210.

The QA environment 204 may run on an application server 214 that may be configured to communicate with the intermediary DB 208 and the vault DB 210. In one embodiment, the application server 214 is a JBOSS JEE application server implementing a JAVA platform in the QA environment 204. The application server 214 may provide a QA request page 218 to the QA user 220 for requesting data migration. The QA user 220 may request for database migration using a user interface (UI) on the QA request page 218. The UI may be a browser based form used to submit a request for migration of data from the production environment 202 to a target environment. The request form may be presented to the QA user 220 using a HTTP browser based communication channel. In one embodiment, the request form includes fields for email address of the requestor and the target environment to which the data should be migrated to.

When the QA user 220 submits a data migration request on the QA request page 218, the information relating to the request is stored in the intermediary database 208 in the QA environment 204. In one embodiment, the date and time of the request is also stored along with the request information in the intermediary database 208.

The data manger 212 is periodically polling for migration requests in the production environment 202. When the migration request is detected by the data manger 212, a one way link 224 is created from the production DB 206 to the intermediary DB 208 through the firewall 222. The data manger 212 generates a snapshot of the production DB 206 for inserting data into the intermediary DB 208 using the one way link 224. Once the snapshot is migrated to the intermediary DB 208, the data manger 212 may destroy the one way link 224 to protect the production environment 202 from unwanted access.

The data loader 216 may periodically check the intermediary DB 208 to determine if a new snapshot needs to be loaded in a target QA environment. In one embodiment of the invention, data is only loaded in the target QA environment if a migration request was made for that target environment. The data loader 216 may load the data from the intermediary DB 208 into the vault DB 210. In one embodiment, the data loader 216 truncates the target database before loading it in the vault DB 210 to ensure that the vault DB 210 is almost identical to the production DB 206 for QA purposes. The data loader 216 may also flag in the intermediary DB 208 that the migration was successful and an email may be generated and sent to the QA user 220 or a detailed log may be generated. In one embodiment, SMTP protocol (Simple Mail Transfer Protocol) may be used for sending the email to the QA user 220 over an IP network.

The QA user 220 now can safely access the vault DB 210 for QA testing purposes without the risk of accessing sensitive consumer information. A single merchant may request different QA target environments for different testing stages. Each target environment may have its own cloned database that the merchant may access for testing specific features of the production DB 206. Different target environments may include target databases for stress testing, functional testing, fraud rules testing, and performance testing and so on.

Figure 3:
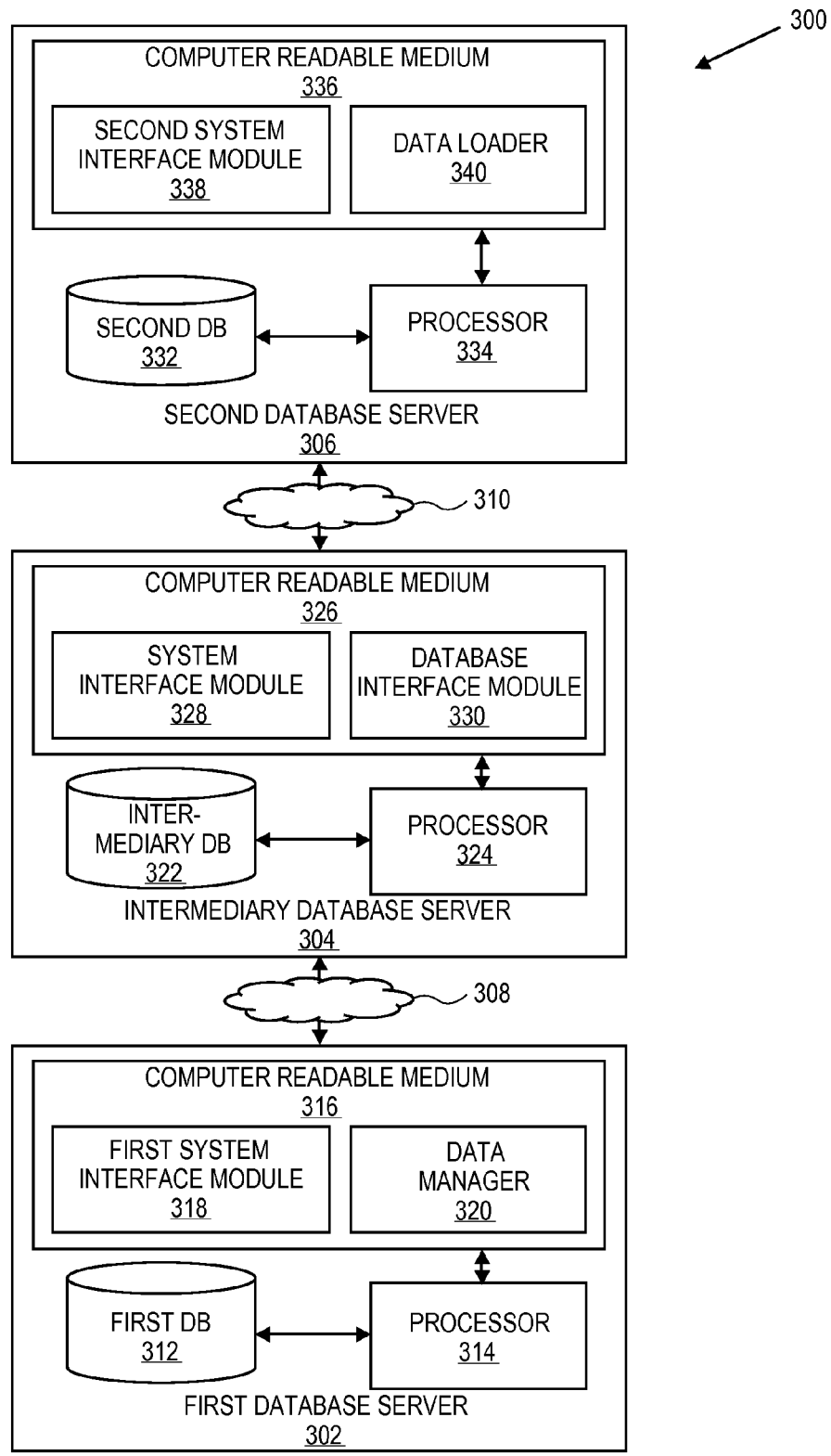
FIG. 3 illustrates certain elements of an exemplary system that may be used to implement embodiments of the invention.

FIG. 3 illustrates certain elements of an exemplary system 300 that may be used to implement embodiments of the invention.

The exemplary system 300 may include a first database server 302, an intermediary database server 304, and a second database server 306. The first database server 302 may include a first DB 312 in a first environment that may have highest level of security and lowest level of privileges from a QA user's perspective, such as QA user 220. In one embodiment, the first database 302 is a production database, such as, production DB 206 residing in production environment 202. The second database server 306 may include a second DB 332 in a second environment that may have lower level of security and higher level of privileges from the QA user's perspective. In one embodiment, the second DB 332 is a QA database, such as, (QA) vault DB 210 residing in QA environment 204. The intermediary database server 304 may include an intermediary DB 322 that may have similar privileges as the second DB 332. In one embodiment, the intermediary DB 322 is the intermediary DB 208 residing in the QA environment 204.

The first database server 302 may communicate with the intermediary database server 304 using a secure network 308. In one embodiment, the secure network may be guarded by a firewall, such as firewall 222. The intermediary database server 304 may communicate with the second database server 306 using a secure network 310. In one embodiment, the intermediary database server 304 and the second database server 306 may reside in the same environment, for example, QA environment 204.

In accordance with aspects of the invention, in response to a migration request to a target environment, data is first migrated from the first DB 312 to the intermediary DB 322 using a secure one way link. In one embodiment, only a subset of the data is transferred from the first DB 312 to the intermediary DB 322. Data from the intermediary DB 322 is then loaded in to the second DB 332 in the target environment. In one embodiment, the data is updated before loading it in to the second DB 332.

The first DB 312 may include sensitive information and data that may be regulated by rules and regulations of a particular industry. Sensitive information may include but is not limited to financial information, medical records, criminal records, vehicle driver information, loan applications, stock trading and voter registration.

The first database server 302 may also include a computer readable medium (CRM) 316 comprising code executable by a processor 314 or processing elements for implementing a method for cloning a database in accordance with aspects of the invention. The computer readable medium 316 may include a first system interface module 318 and a data manager 320. In one embodiment, the data manager 320 is similar to the data manager 212 residing in the production environment 202. The data manager 320 may be configured to poll the intermediary DB 322 for a migration request for migrating the first DB 312 to the second DB 332. In response to the polling, the data manager 320 detects the migration request and creates a link from the first DB 312 to the intermediary DB 322 through the communication network 308. The data manager 320 further generates a snapshot of the first DB 312 and migrates the data into the intermediary DB 322 using the link. Once the data is migrated to the intermediary DB 322, the data manager 320 may destroy the link between the first DB 312 and the intermediary DB 322.

The first system interface module 318 may be configured to communicate with a system administrator for setting up scripts for launching data manager 320 on the first database server 302. In one embodiment, the system administrator may create a crontab entry for the data manager 320 to execute at regular intervals. Note that proper permissions may be required to create crontab entry for the data manager 320. In some embodiments, the data manager 320 may execute DDL scripts to create and destroy the link. In one embodiment, the DDL is executed on an Oracle production database so that a database link to QA Oracle instance may be created. In one embodiment, the snapshot is captured by executing embedded SQL (Structured Query Language) using a JDBC (Java Database Connectivity) application programming interface (API). The embedded SQL may be an INSERT only function from the first DB 312 to the intermediary DB 322 to ensure the one way link.

The intermediary database server 304 may also include a computer readable medium 326 comprising code executable by a processor 324 or processing elements for implementing a method for cloning a database in accordance with aspects of the invention. The computer readable medium 326 may include a system interface module 328 and a database interface module 330. The intermediary database server 304 is configured to communicate with the second database server 306 using a network 310.

The system interface module 328 may be configured to communicate with the system administrator for receiving migration requests from QA users and storing information relating to the migration requests in the intermediary DB 322.

In one embodiment, the information stored in the intermediary DB 322 may include email address of the requestor, target environment, date and time of the request, date and time the request was completed, remote user identifier that initiated the request and IP address of the remote user that initiated the request.

The database interface module 330 may be configured to communicate with the first database server 302 and the second database server 306. In one embodiment, the database interface module 330 may receive a first query from the first database server 302 for the migration requests stored in the intermediary DB 322. In response to the first query, a snapshot of the first DB 312 may be stored in the intermediary DB 322 using the one way link generated by the data manager 320. The database interface module 330 may further receive a second query from the second database server 306 for migrating snapshot data into the second DB 332. In response to the second query, the data is migrated to the second database server 306 for loading into the second DB 332.

The second database server 306 may also include a computer readable medium 336 comprising code executable by a processor 334 or processing elements for implementing a method for cloning a database in accordance with aspects of the invention. The computer readable medium 336 may include a second system interface module 338 and a data loader 340.

The data loader 340 may be configured to periodically check whether any new snapshots need to be loaded in to a target QA environment. Data shall be loaded only when a request was made for a target environment. The data loader may extract the target environment from the migration request. The data loader then updates the target environment QA database (Vault database). Data loader 340 imports the data from the intermediary DB 322 into the second DB 332. In one embodiment, the data loader 340 updates the data before loading it into the second DB 332. In some embodiments, the data loader 340 truncates the data before loading into the second DB 332.

The second system interface module 338 may be configured to notify the requestor of the migration request that the migration is complete. In one embodiment, an email is sent to the requestor at the email address provided with the migration request. The data loader 340 further updates a status flag in the intermediary DB 322 that the migration is successful for the specific migration request.

Embodiments of the invention allow cloning a production database into a target environment so that only partial access to the sensitive information is available by a user who needs to access this information for testing purposes.

Database migration process may require necessary privileges granted in the local and the remote databases irrespective of whether the local and remote are different user accounts. Database link creation can be created using separate accounts. It does not have to have same user password established on local and remote databases.

Figure 4:
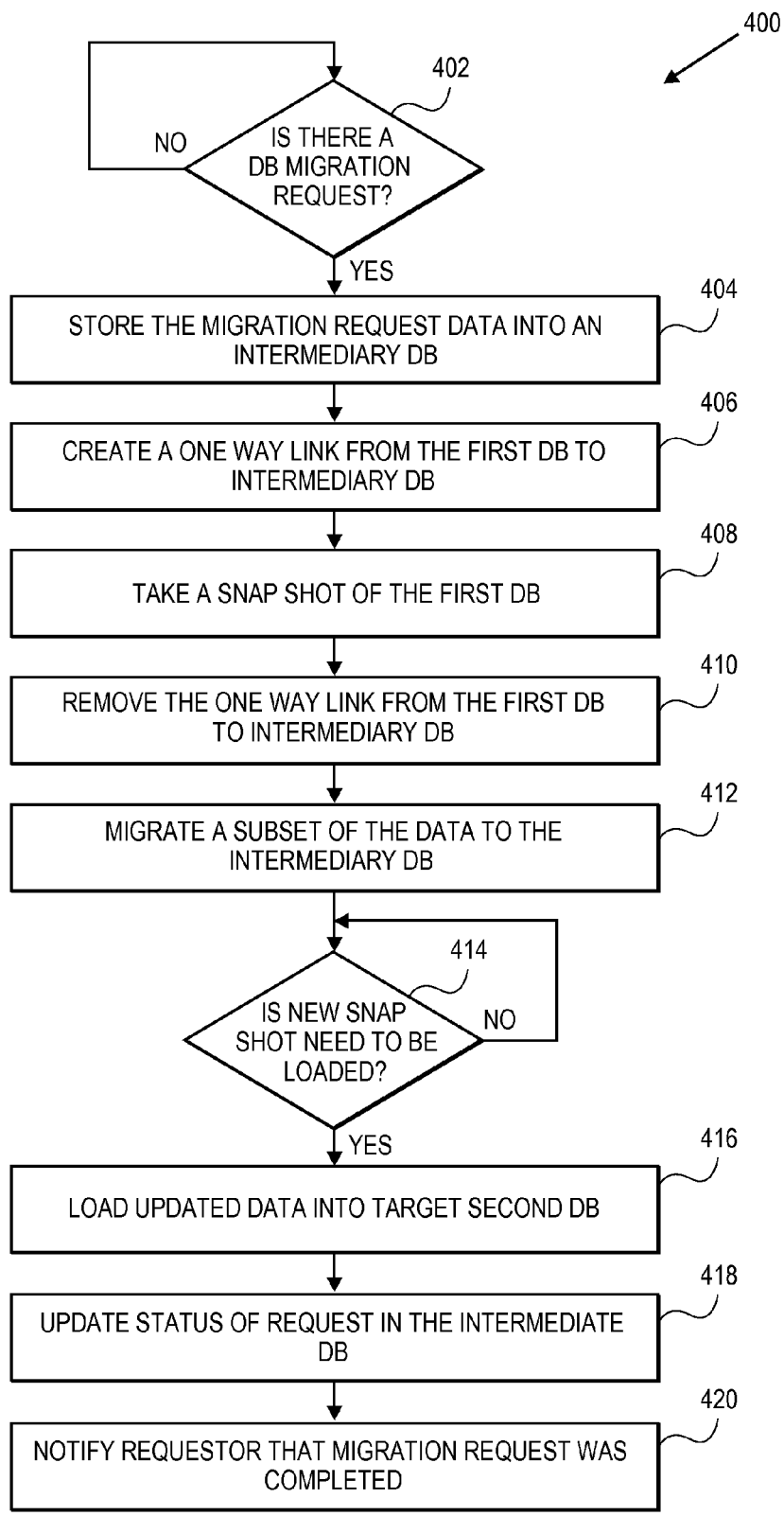
FIG. 4 illustrates an exemplary flow diagram, illustrating a method for migrating a production database to a QA database in a target environment.

FIG. 4 illustrates an exemplary flow diagram, illustrating a method for migrating a database to a target environment.

At step 402, the data manager 320 checks to see if a data migration was requested by polling the intermediary DB 322. If there is no request for data migration, the data manager 320 goes to sleep for a pre-determined duration and checks for the migration request again once the duration expires. The data migration request may be initiated by the QA user 220 using a browser based interface. The request may include the email address of the requestor and the target environment to which the data should be migrated to.

At step 404, the information relating to the data migration request is stored in the intermediary DB 322. In one embodiment, the information stored relating to the migration request includes the email address of the requestor, the target environment, date and time of the request, date and time the request was completed, remote user identifier who initiated the request and the IP address of the remote user who initiated the request.

At step 406, the data manager 320 creates a one-way link from the first DB 312 to the intermediary DB 322 using the secure network 308. In one embodiment, the database link is created by executing a DDL script on the first database server 302. In case the DDL script fails to create the link due to incorrect permissions, an error log may be generated or an email may be sent to the system administrator. An email to the QA user 220 may also be sent specifying that a particular migration request failed and information regarding the failure. An error message may also be sent to the intermediary DB 322 indicating that the migration for specific request failed.

At step 408, the data manager 320 may create a snapshot of the first DB 312. In one embodiment, the snapshot may be generated using an embedded SQL on the first database 312. The embedded SQL may be an INSERT only function from the first (production) environment to the second (QA) environment in order to ensure a unidirectional link between the two databases.

At step 410, the data manager 320 may remove the unidirectional link between the first DB 312 and the intermediary DB 322. As with the step 406, the link may be removed using a DDL script.

At step 412, the data manager 320 may migrate the data to the intermediary DB 322 destined for the target environment. In one embodiment, only a subset of the data from the first DB 312 is migrated. As an example, for payment systems, only tokens, credit card type and some other related information is migrated to the target environment but the PAN is not migrated.

At step 414, the data loader 340 may poll the intermediary DB 322 to check if a new snapshot needs to be loaded into the target QA environment. Only if a request was made for migration to a target environment, the data loader 340 initiates the data loading.

At step 416, the data loader 340 may import data from the intermediary DB 322 for loading into the second DB 332. In some embodiments, the data loader 340 updates the data before loading it into the target environment. For example, in payments fake payment card numbers may be generated and each row entry is encrypted before loading it in to the target environment. In one embodiment, the data loader 340 truncates target QA database before loading new data.

At step 418, the data loader 340 updates the status of the migration request in the intermediary DB 322 as to provide updated record of migration execution.

At step 420, the data loader 340 notifies the requestor that the migration request was completed. In one embodiment, an email is sent to the requestor at the email address provided in the migration request.

Figure 5:
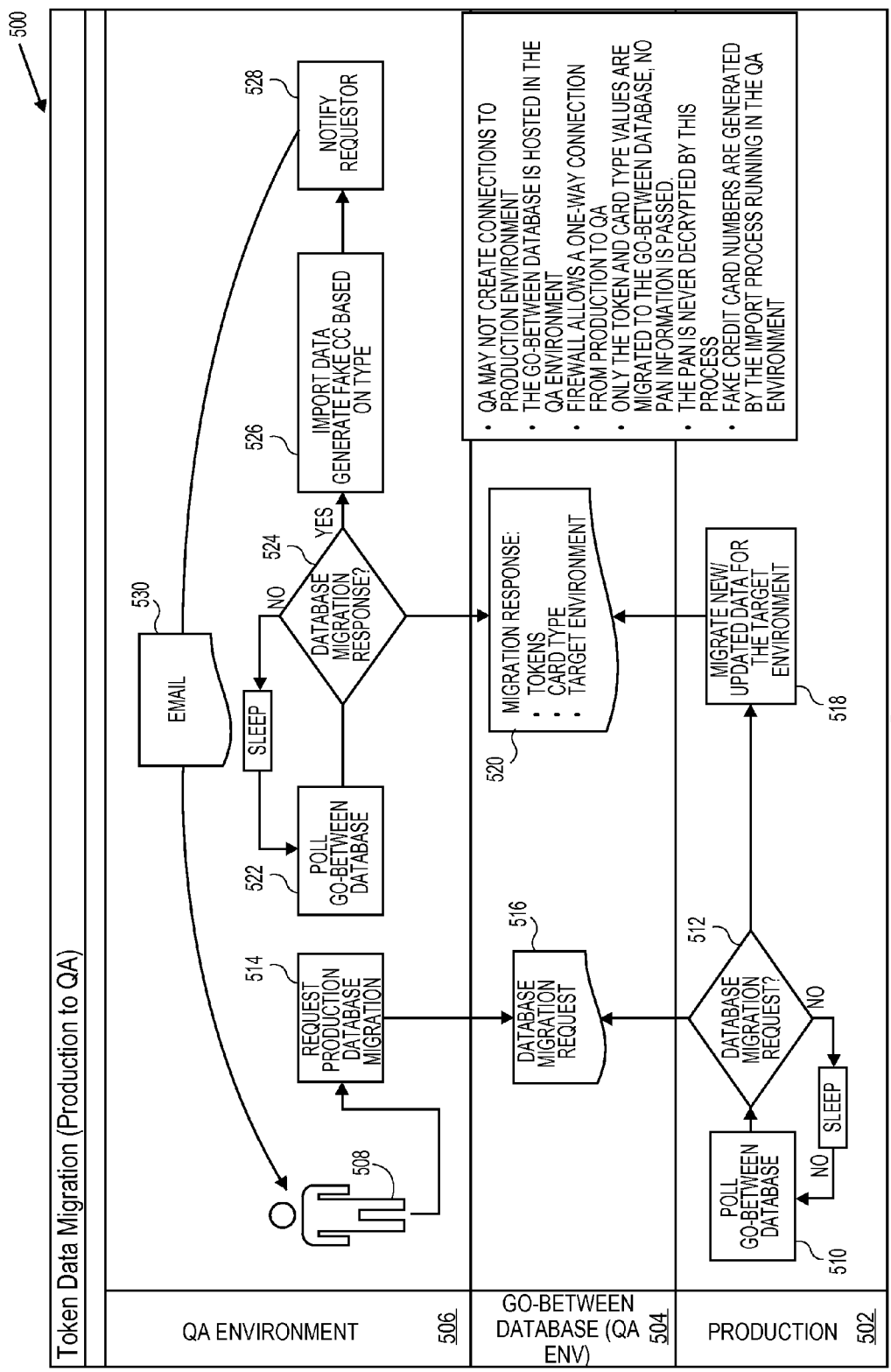
FIG. 5 illustrates an exemplary flow diagram, illustrating a non-limiting embodiment of the invention for cloning a production database for quality assurance.

FIG. 5 is a system 500 illustrating a non-limiting embodiment of the invention for migrating a production database from a production environment to a QA environment for quality assurance.

A production database, such as, production DB 206 may be residing in a production environment 502 that needs to be migrated to a QA environment 506. The production database may include data relating to financial records for plurality of customers. In one embodiment, the production data may include customers' credit card information (PAN, token, card type, etc.) and personal information (name, address, phone number, etc.).

The production environment 502 may have the highest level of security and lowest level of privileges from the end-user, QA user or merchant's perspective. To comply with the PCI rules, the production environment 502 and all consumer data associated with the production environment 502 are maintained in strict isolation from the QA environment 506. The intermediary database environment 504 has lower privilege restrictions. For instance, the intermediary DB 322 may have requests pending from the QA user 220 in the intermediary database environment 504. In some instances, the QA user 220 may also have access or enough influence on code running in the intermediary database environment. In one aspect of the invention, the intermediary database environment 504 is considered part of the QA environment 506. The QA user 220 or the merchant has a higher level of access in the QA environment 506.

At step 510, a data manager module (for example, data manager 320) in a production environment 502 is polling for database migration requests. When there is no database requests received, the data manager module goes to sleep for a pre-determined duration.

At step 510, the data manager module in the production environment 602 queries an intermediary (go-between) environment 504 for database migration requests. The terms "go-between" and "intermediary" are used interchangeably throughout the application.

At step 514, a QA user 508 submits a request for database migration from the production environment 502 to a QA environment 506. In one embodiment, the QA user 508 uses a web based form to submit the request. The migration request may include the email address of the requestor and the target environment to which the data should be migrated.

At step 516, the database migration request is stored in an intermediary DB in the intermediary environment 504. The data manager module detects the migration request stored in the intermediary DB.

At step 518, the data manager module migrates updated data for the target environment in to an intermediary DB in the intermediary environment 504. The updated data may include the tokens, card type values and the target environment. No PAN information is passed from the production environment 502 to the go-between environment 504. In one embodiment, a unidirectional link is created from the production environment 502 to the go-between environment 504 through a firewall.

At step 520, a snapshot of the production DB is created in the intermediary database. The data manager module removes the one way link between the production environment 502 and the go-between environment 504.

At step 522, a data loader module (for example, data loader 340) is polling the go-between environment 504 for the database migration response. In the absence of a response, the data loader module goes to sleep for a pre-determined duration of time.

At step 524, the data loader module detects that a new snapshot is ready to be loaded in a target environment. Note that the new snapshot may only be loaded if there was a migration request for that target environment.

At step 526, the data loader module imports the snapshot data in a QA database in the target environment. In one embodiment, the data loader module generates fake payment card number (for example, fake credit card number) for each row based on the card type value. The data loader module further generates a stream of data for each row and batch loads data into the targeted QA environment. In one embodiment, the data loader module encrypts each data entry before inserting into specific QA environment database. In some embodiments, the data loader module may truncate the target database before loading it into the QA database.

At step 528, the requestor is notified that the data migration is complete. In one embodiment, an email 530 is sent to the QA user 508.

Figure 6:
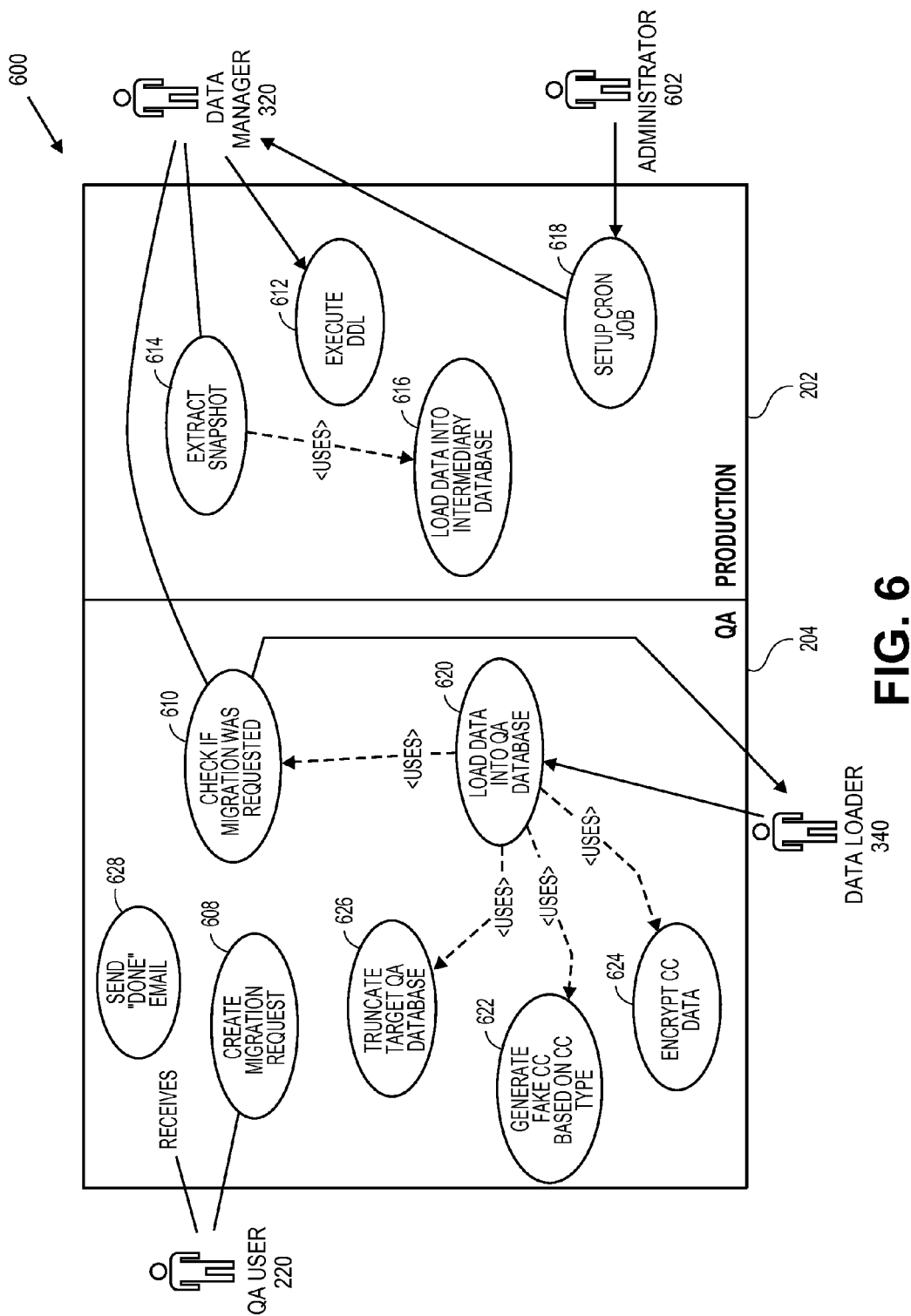
FIG. 6 is a block diagram illustration of an embodiment of the invention showing the various modules in the system and their respective interaction.

FIG. 6 is an illustration of an embodiment of the invention showing the various modules in the system and their respective interaction. The elements in FIG. 6 are further described with respect to FIGS. 7-10.

Figure 7:
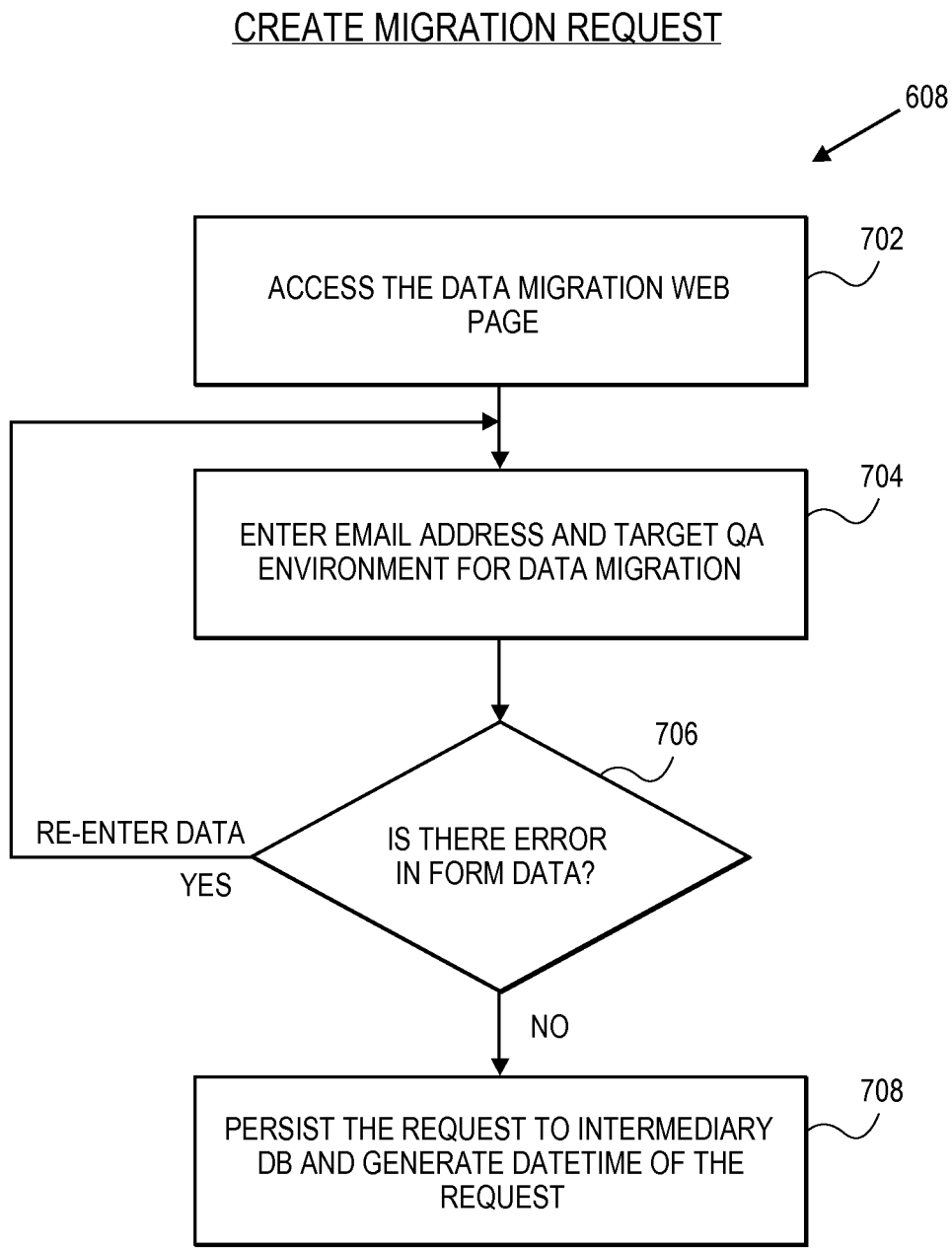
FIG. 7 illustrates an exemplary use case flow diagram for creating a migration request.

The QA user 220 creates a migration request 608 in the QA environment 204, as described further using FIG. 7.

FIG. 7 illustrates an exemplary use case flow diagram for creating a migration request.

At step 702, the QA user 220 accesses a data migration web page to fill in a data migration request form. In one embodiment, SiteMinder Single Sign-on (SSO) application executing on the application server 214 may be used for authentication and signing on to the data migration web page.

At step 704, the QA user 220 provides an email address and a target QA environment for data migration from the production environment 202 to the QA environment 204.

At step 706, a web application running on the application server 214 may validate the data migration request form data to check for errors. If an error is found, an error page may be displayed with the details of the error occurrence and the QA user 220 is allowed to re-enter the data at step 704. The QA user 220 corrects the data and the web application validates that no errors are found.

At step 708, the web application takes the form data and generates date and time of request and persists the request to the intermediary database 322. The intermediary database 322 will be the decision provider for any process needing to know if a migration needs to occur and also the target environment to which the data should be migrated to and its status.

Figure 8:
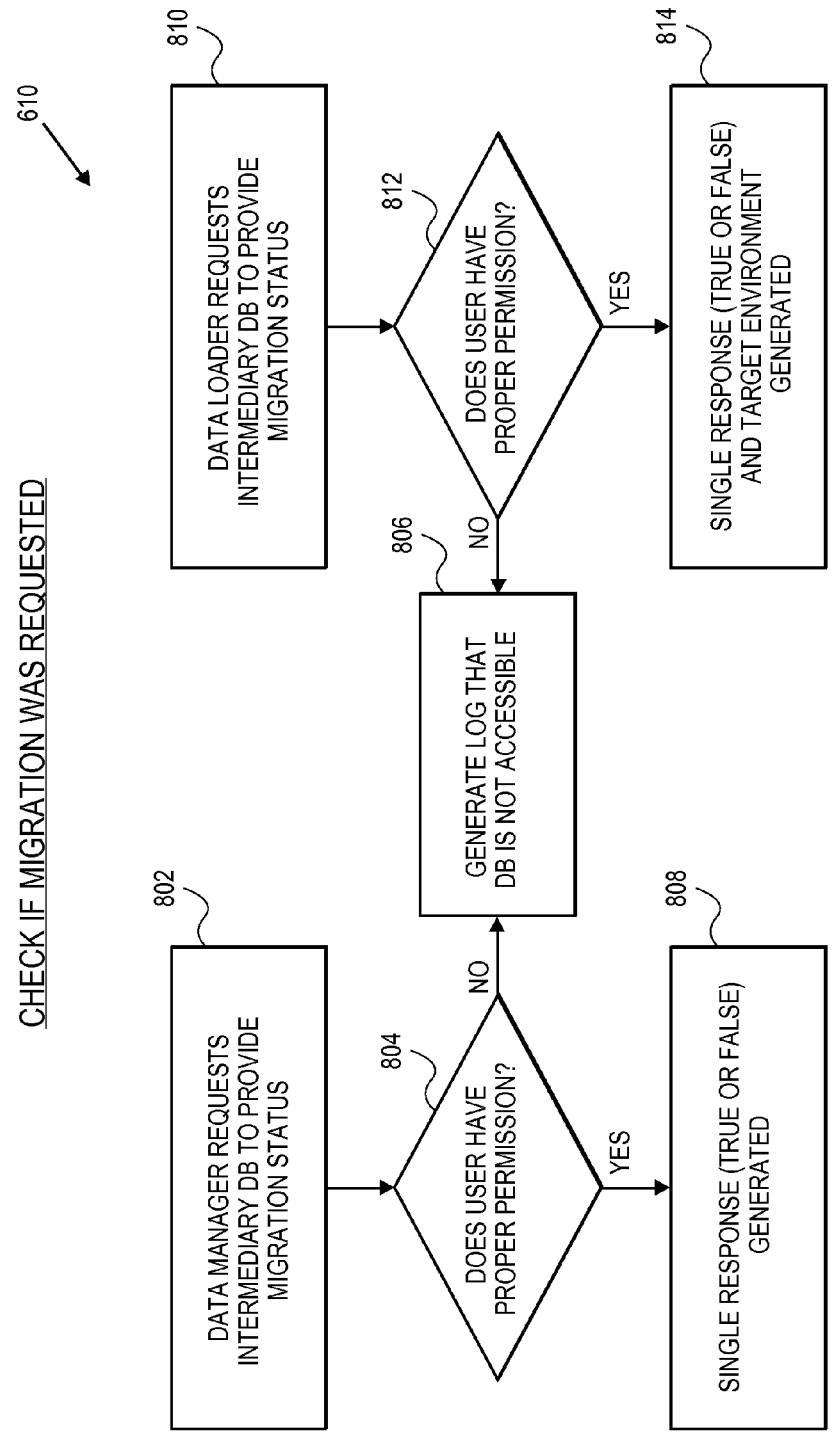
FIG. 8 illustrates an exemplary use case flow diagram for checking if migration was requested.

Referring back to FIG. 6, a process 610 checks if migration was requested, as described further using FIG. 8.

FIG. 8 illustrates an exemplary use case flow diagram for checking if migration was requested. A common interface is provided that allows a module (data manager 320 or data loader 340) to check if migration is to occur and on which environment.

At step 802, the data manger 320 requests the intermediary DB 322 to provide migration status.

At step 804, the data manger 320 checks to see if the user has proper permissions to access the intermediary DB 322.

At step 806, if the user does not have proper permissions to access the intermediary DB 322, an error log is generated that DB is not accessible or an email to the QA user 220 is sent.

At step 808, if the intermediary DB 322 is accessible, a response with the migration status is generated.

At step 810, the data loader 340 requests the intermediary DB 322 to provide migration status and the target environment.

At step 812, the data loader 340 checks to see if the user has proper permissions to access the intermediary DB 322.

At step 814, if the intermediary DB 322 is accessible, a response with the migration status and the target environment is generated.

Referring back to FIG. 6, the data manager 320 may execute DDL scripts via CLI (Common Language Infrastructure) so that a database link between the production DB 312 and the intermediary DB 322 may be established, SQL may be executed for generating a snapshot of the production DB 312 and database link between the production DB 312 and the intermediary DB 322 may be destroyed. A process 612 for executing DDL is described further using FIG. 9.

Figure 9:
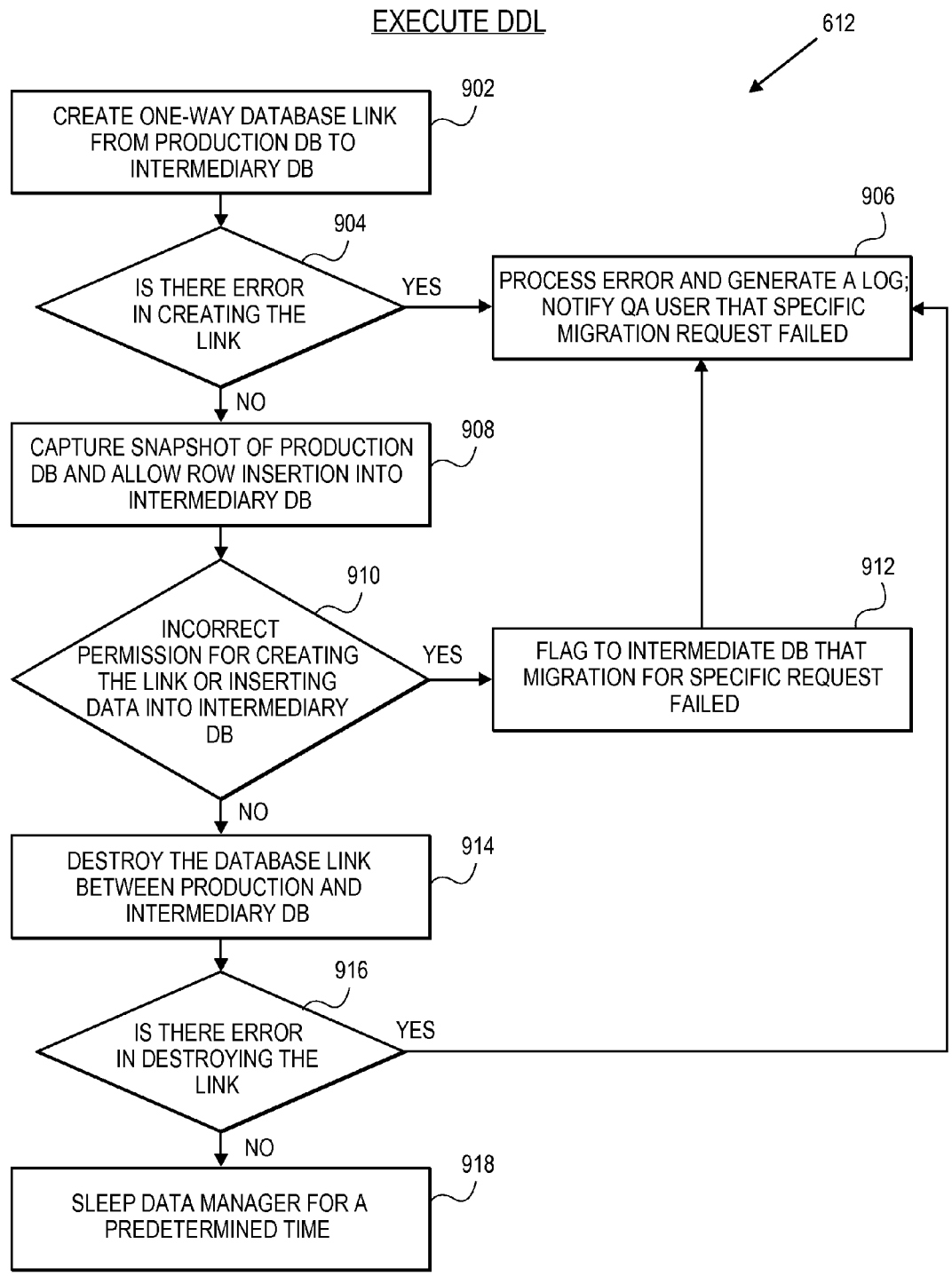
FIG. 9 illustrates an exemplary use case flow diagram for executing a DDL (Data Description language) application.

FIG. 9 illustrates an exemplary use case flow diagram for executing a DDL application.

At step 902, a one way link from the production DB 312 to the intermediary DB 322 is created.

At step 904, the data manger 320 checks whether there was an error in creating the link.

At step 906, the data manger 320 processes the error and generates a log message or an email with details. The data manger 320 also sends an email to the QA user 220 that a specific migration request failed specifying the nature of why the process failed.

At step 908, the data manger 320 executes a process 614 to extract snapshot of the production DB 312. In one embodiment, the snapshot of the production DB 312 is extracted using embedded SQL (JDBC). The data manger 320 further executes a process 616 to load data into the intermediary DB 322.

At step 910, the data manger 320 checks to see if there is incorrect permissions in creating the link or inserting data into the intermediary DB 322.

At step 912, the data manger 320 flags to the intermediary DB 322 that migration for the specific request failed and goes back to step 906.

At step 914, the data manger 320 destroys the link between the production DB 312 and the intermediary DB 322.

At step 916, the data manger 320 checks if there is error in destroying the link it goes back to step 906.

At step 918, the data manger 320 goes to sleep for a pre-determined period of time before polling for migration request again.

Referring back to FIG. 6, an administrator 602 may setup a cron job process 618 to execute the data manager 320 at regular intervals. Once the snapshot is loaded in the intermediary DB 322, the data loader will execute a process 620 to load data in to QA database, as discussed with the help of FIG. 10.

Figure 10:
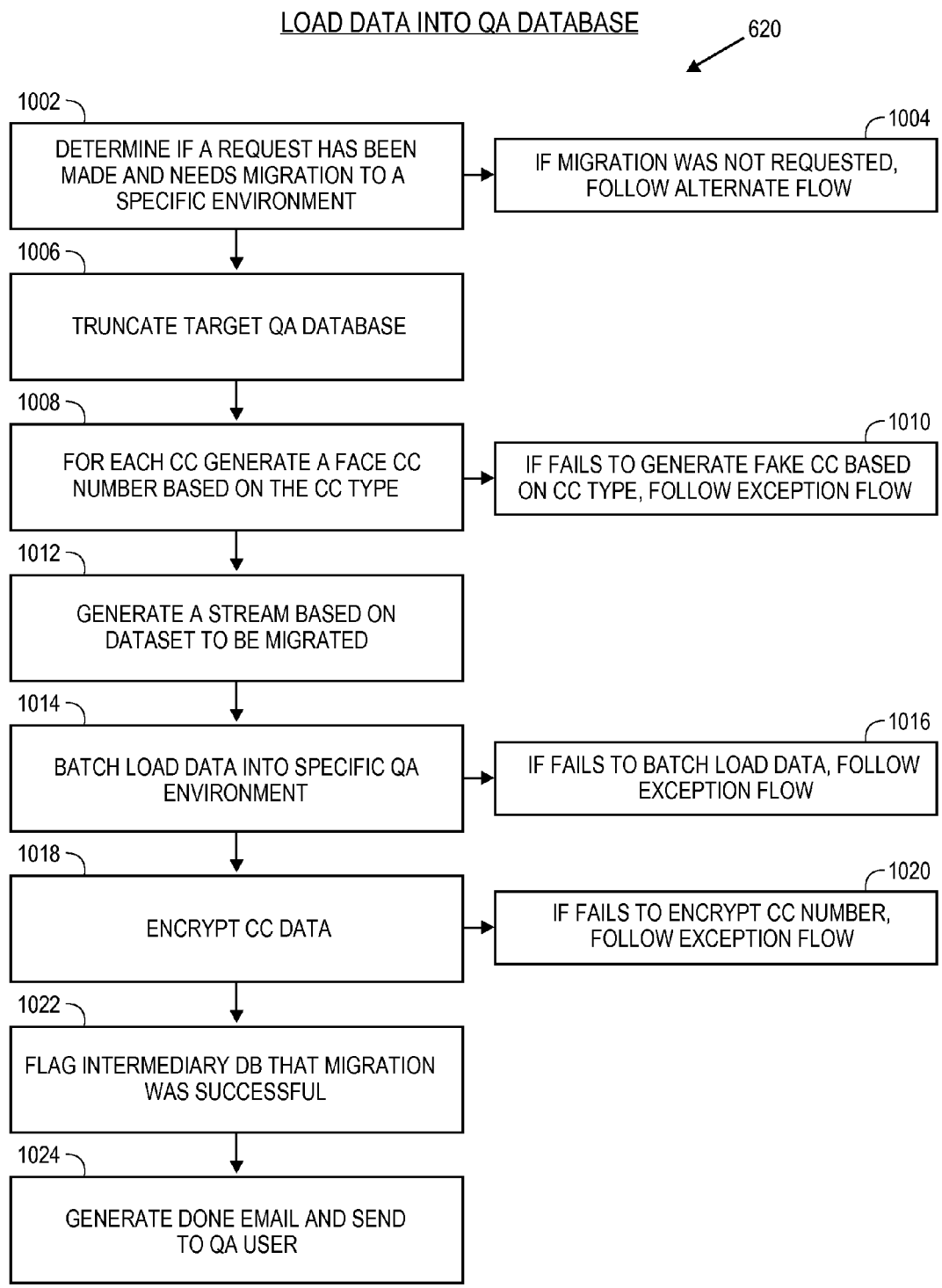
FIG. 10 illustrates an exemplary use case flow diagram for loading data into a QA database.

FIG. 10 illustrates an exemplary use case flow diagram for loading data into a QA database.

At step 1002, the data loader 340 determines if a request for migration has been made for a specific target environment.

At step 1004, if the data loader 340 determines that the migration request was not made, an alternate flow is followed where the data loader 340 sleeps for a certain pre-determined duration before checking again.

At step 1006, the data loader 340 executes a process 626 to truncate target QA database.

At step 1008, the data loader 340 executes a process 622 to generate a fake CC (credit card) number based on the CC type for each CC row. Note that for exemplary purposes, a credit card is used; however, any payment card such as debit, stored value or credit card may be used.

At step 1010, if the data loader 340 fails to generate fake CC number based on the CC type, an exception flow is followed by logging the rows that generated the error.

At step 1012, the data loader 340 generates a stream based on data set to be migrated.

At step 1014, the data loader 340 batch loads the data into specific QA environment.

At step 1016, if the data loader 340 fails to batch load the data, an exception flow is followed to proceed with the next batch. If all the batches fail then a "failure" is reported otherwise a "partial failure" is reported.

At step 1018, the data loader 340 executes a process 624 to encrypt the CC column for each row inserted into specific QA environment database.

At step 1020, if the data loader 340 fails to encrypts the CC column, an exception flow is followed by reporting "partial failure".

At step 1022, the data loader 340 flags to the intermediary DB 340 that the migration was successful.

At step 1024, the data loader 340 executes a process 628 to send a "done" email to the QA user at the email address provided with the migration request.

For all the "failure" and "partial failure" results, an email is sent to the QA user with the log. A "partial failure" may force a reload of data however remediation at the intermediary DB 322 may be required.

The above described embodiments of the invention are not limited to protecting sensitive information in a payment network, but are extendable to any environment that requires quality assurance or validation of the environment infrastructure with sensitive information. Embodiments of the invention maybe used to protect sensitive information such as social security numbers, medical records, criminal records, vehicle driver information, loan applications, stock trading and voter registration instead of payment account numbers described above.

Figure 11:
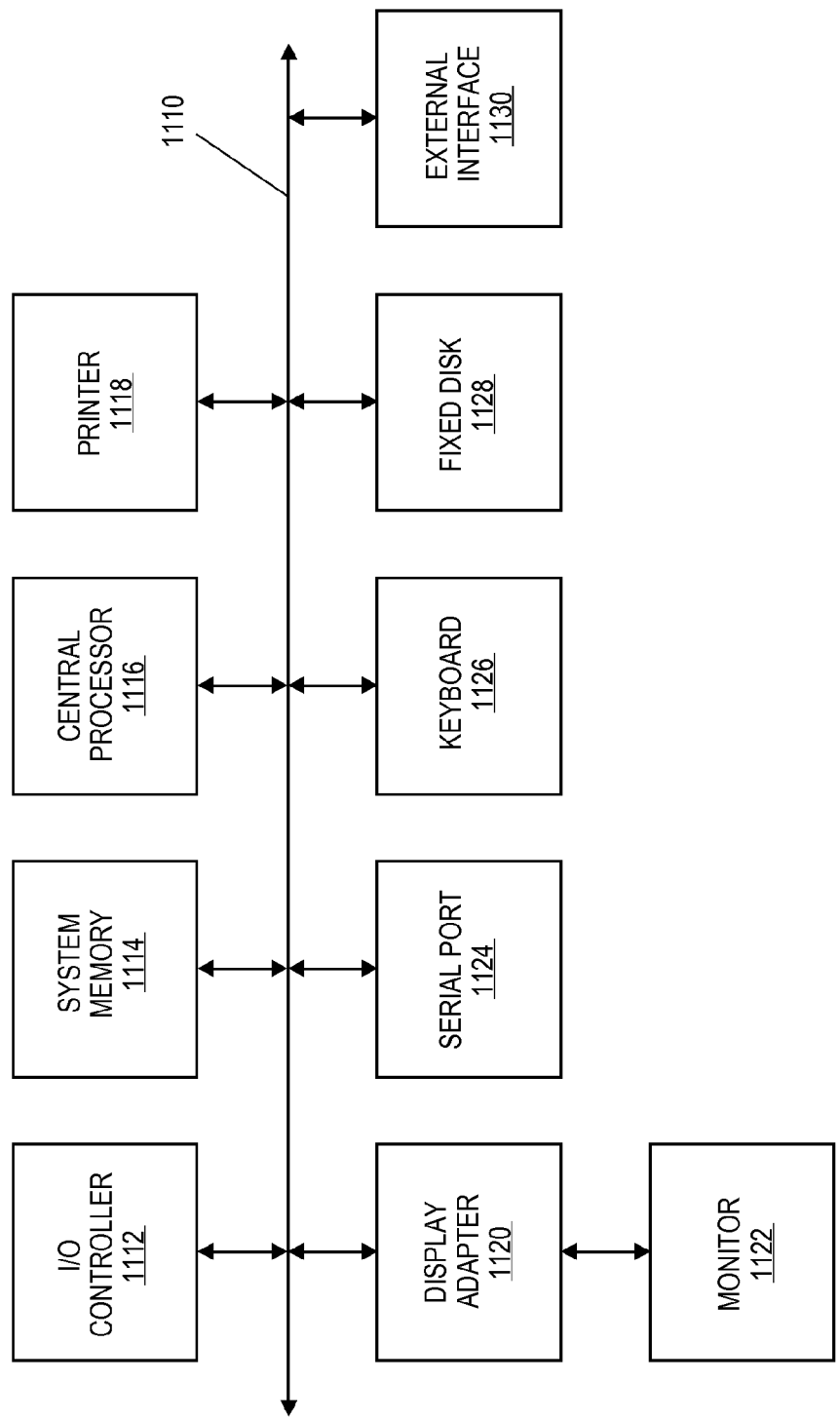
FIG. 11 shows a system diagram according to an embodiment of the invention.

FIG. 11 shows a system diagram according to an embodiment of the invention.

FIG. 11 is a high level block diagram of a computer system that may be used to implement any of the entities or components described above. The subsystems shown in FIG. 11 are interconnected via a system bus 1102. Additional subsystems include a printer 1110, keyboard 1118, fixed disk 1120, and monitor 1112, which is coupled to display adapter 1114. Peripherals and input/output (I/O) devices, which couple to I/O controller 1104, can be connected to the computer system by any number of means known in the art, such as a serial port. For example, serial port 1116 or external interface 1122 can be used to connect the computer apparatus to a wide area network such as the Internet, a mouse input device, or a scanner. The interconnection via system bus 1102 allows the central processor 1108 to communicate with each subsystem and to control the execution of instructions from system memory 1106 or the fixed disk 1120, as well as the exchange of information between subsystems. The system memory 1106 and/or the fixed disk may embody a computer-readable medium.

As described, the inventive service may involve implementing one or more functions, processes, operations or method steps. In some embodiments, the functions, processes, operations or method steps may be implemented as a result of the execution of a set of instructions or software code by a suitably-programmed computing device, microprocessor, data processor, or the like. The set of instructions or software code may be stored in a memory or other form of data storage element which is accessed by the computing device, microprocessor, etc. In other embodiments, the functions, processes, operations or method steps may be implemented by firmware or a dedicated processor, integrated circuit, etc.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may reside on or within a single computational apparatus, and may be present on or within different computational apparatuses within a system or network.

While certain exemplary embodiments have been described in detail and shown in the accompanying drawings, it is to be understood that such embodiments are merely illustrative of and not intended to be restrictive of the broad invention, and that this invention is not to be limited to the specific arrangements and constructions shown and described, since various other modifications may occur to those with ordinary skill in the art.

As used herein, the use of "a", "an" or "the" is intended to mean "at least one", unless specifically indicated to the contrary.

What is claimed is:

1. A computer implemented method for migrating a database comprising:
    receiving a migration request for migrating a first database associated with a first database server to a second database associated with a second database server, wherein the migration request comprises information specifying a target environment of the second database server and information identifying a requestor that sent the migration request;
    storing the migration request in an intermediary database associated with an intermediary database server;
    receiving a first query from the first database server for the migration request stored in the intermediary database;
    receiving, at the intermediary database, a snapshot of the first database from the first database server using a link between the first database and the intermediary database, the link created by the first database server;
    storing the snapshot of the first database in the intermediary database;
    receiving a second query from the second database server for migrating snapshot data into the second database; and
    migrating the snapshot data from the intermediary database for loading into the second database for use in the target environment, in response to the second query.

2. The computer implemented method of claim 1, wherein the link created by the first database server is a one-way link from the first database to the intermediary database.

3. The computer implemented method of claim 1, wherein loading the snapshot data from the intermediary database into the second database comprises determining that a request for migration was received before loading the snapshot data into the second database.

4. The computer implemented method of claim 1, wherein the migration request is submitted using a browser-based form.

5. The computer implemented method of claim 1, wherein a status of the migration request is updated in the intermediary database as a result of migration.

6. An intermediary database server, comprising:
    a processor;
    a computer-readable medium coupled to the processor, wherein the computer-readable medium comprises code executable by the processor for implementing a method for migrating a database, the method comprising:
        receiving a migration request for migrating a first database associated with a first database server to a second database associated with a second database server, wherein the migration request comprises information specifying a target environment of the second database server and information identifying a requestor that sent the migration request;
        storing the migration request in an intermediary database associated with an intermediary database server;
        receiving a first query from the first database server for the migration request stored in the intermediary database;
        receiving, at the intermediary database, a snapshot of the first database from the first database server using a link between the first database and the intermediary database, the link created by the first database server;
        storing the snapshot of the first database in the intermediary database;
        receiving a second query from the second database server for migrating snapshot data into the second database; and
        migrating the snapshot data from the intermediary database for loading into the second database for use in the target environment, in response to the second query.

7. An intermediary database server, comprising:
    a processor;
    a computer-readable medium coupled to the processor, wherein the computer-readable medium comprises code executable by the processor for implementing a method for migrating a database, the method comprising:
        receiving a migration request for migrating a first database associated with a first database server to a second database associated with a second database server;
        storing the migration request in an intermediary database associated with the intermediary database server;
        receiving a first query from the first database server for the migration request stored in the intermediary database;
        storing a snapshot of the first database in the intermediary database, after receiving the first query, using a link created by the first database server;
        receiving a second query from the second database server for migrating snapshot data into the second database; and
        migrating the snapshot data from the intermediary database for loading into the second database in response to the second query, wherein the snapshot data includes a plurality of payment tokens, card types and a target environment.

8. The intermediary database server of claim 6, wherein the snapshot data is updated before loading into the second database.

9. An intermediary database server, comprising:
    a processor;
    a computer-readable medium coupled to the processor, wherein the computer-readable medium comprises code executable by the processor for implementing a method for migrating a database, the method comprising:
        receiving a migration request for migrating a first database associated with a first database server to a second database associated with a second database server;
        storing the migration request in an intermediary database associated with the intermediary database server;

receiving a first query from the first database server for the migration request stored in the intermediary database;

storing a snapshot of the first database in the intermediary database, after receiving the first query, using a link created by the first database server;

receiving a second query from the second database server for migrating snapshot data into the second database; and migrating the snapshot data from the intermediary database for loading into the second database in response to the second query, wherein the snapshot data is updated before loading into the second database, and wherein updating the snapshot data includes generating fake credit card numbers.

10. The intermediary database server of claim 6, wherein all snapshot data encrypted before loading into the second database.

11. The computer implemented method of claim 1, further comprising:

removing the link between the first source database and the intermediate database after receiving the snapshot of the first database at the intermediary database.

12. The computer implemented method of claim 1, further comprising:

receiving, by the requestor, a notification that the snapshot data was successfully migrated from the intermediary database to the second database.

13. The computer implemented method of claim 12, wherein the notification comprises an email.

14. The computer implemented method of claim 1, further comprising:

determining by the first database server if the requestor has the proper permissions to access the intermediary database.

15. The computer implemented method of claim 14, further comprising:

generating by the server database server an error log that the requestor has does not have the proper permissions to access the intermediary database.

16. The intermediary database server of claim 6, further comprising:

removing the link between the first source database and the intermediate database after receiving the snapshot of the first database at the intermediary database.

17. The computer implemented method of claim 1, wherein the target environment of the second database server comprises a quality assurance environment for functional testing of the first database.

18. The intermediary database server of claim 6, wherein the target environment of the second database server comprises a quality assurance environment for functional testing of the first database.

19. The intermediary database server of claim 6, further comprising:

determining by the first database server if the requestor has the proper permissions to access the intermediary database.

20. The intermediary database server of claim 6, wherein the link between the first database and the intermediate database passes through a firewall.

* * * * *